United States Patent [19]
Miyashita et al.

[11] Patent Number: 5,271,796
[45] Date of Patent: Dec. 21, 1993

[54] METHOD AND APPARATUS FOR DETECTING DEFECT ON SEMICONDUCTOR SUBSTRATE SURFACE

[75] Inventors: Moriya Miyashita, Yokohama; Mokuji Kageyama; Hachiro Hiratsuka, both of Yokohama, all of Japan

[73] Assignee: Kabushiki Kaisha Toshiba, Kawasaki, Japan

[21] Appl. No.: 858,700

[22] Filed: Mar. 27, 1992

[30] Foreign Application Priority Data

Mar. 27, 1991 [JP] Japan .................................. 3-63586

[51] Int. Cl.⁵ .................... H01L 21/306; B44C 1/22
[52] U.S. Cl. .................... 156/626; 156/651; 156/654; 156/662; 156/345; 252/79.5
[58] Field of Search .............. 156/626, 627, 651, 654, 156/657, 662, 345; 252/79.5; 356/388, 390, 445, 448

[56] References Cited
U.S. PATENT DOCUMENTS
4,243,473  1/1981  Yamaguchi et al. ................ 156/626

FOREIGN PATENT DOCUMENTS
0247771  7/1987  Fed. Rep. of Germany ...... 156/626
59-75640  4/1984  Japan .................................. 156/626
0122648  6/1986  Japan .................................. 156/626

OTHER PUBLICATIONS
Miyashita et al. (1991) *Electrochem. Soc. Extended Abstracts* 91-1:286-287, Abstract No. 204: Origin of Surface Micro Defect on Annealed Silicon Wafer.

Primary Examiner—William A. Powell
Attorney, Agent, or Firm—Foley & Lardner

[57] ABSTRACT

A method of detecting a defect on the surface of a semiconductor substrate, including: a first etching step of etching a semiconductor substrate by a first etching amount; a first check step of applying a beam to the surface of the substrate underwent the first etching step, and detecting a first reflected beam; a second etching step of etching the substrate etched by the first etching amount, by an additional etching amount, to make the total etching amount a second etching amount; a second check step of applying the beam to the surface of the substrate underwent the second etching step, and detecting a second reflected beam; and a calculation step of calculating the relation between the first and second reflected beams.

20 Claims, 7 Drawing Sheets

METHOD AND APPARATUS FOR DETECTING DEFECT ON SEMICONDUCTOR SUBSTRATE SURFACE

FIELD OF THE INVENTION

The present invention relates to a method of evaluating semiconductor substrates and an apparatus for practicing the method, and a standard substrate suitable for calibration of such an apparatus and a method of manufacturing the same.

BACKGROUND OF THE INVENTION

A semiconductor integrated circuit is formed on a semiconductor substrate (wafer). The quality of the crystal property not only within the wafer but also near the wafer surface plays an important role. Accordingly, the crystal property on the wafer surface and near the surface affecting the property on the surface has been evaluated. Most of such evaluation relies upon the deterioration degree of crystal property such as stacking fault and slip caused by thermal treatment accompanied by oxidation or diffusion, and upon the amount of precipitated substances caused by solid-solution oxygen near the surface.

With the above-described conventional evaluation method, thermal treatment similar to the actual semiconductor device manufacturing process is required, unable to provide correct evaluation.

Electrical characteristics such as junction leakage are important for highly integrated DRAMs. Such electrical characteristics are influenced by crystal defects near the surface which is so fine as to be difficult to be detected by the above-described conventional evaluation method. A distinct difference of yield between devices appears even by using wafers evaluated by the conventional method as having no significant difference.

SUMMARY OF THE INVENTION

The present invention has been made in consideration of the above circumstances. It is an object of the present invention to provide a method and apparatus capable of evaluating semiconductor substrates by detecting crystal defects influencing product yield without performing a thermal treatment similar to an actual semiconductor device manufacturing process, and to provide a standard substrate for use in calibrating such an apparatus and a method of manufacturing such a standard substrate.

As a semiconductor substrate is etched, the diameter of a concave as a defect on the substrate surface becomes large in correspondence with the etching amount. Therefore, the diameter of a concave etched by a certain etching amount differs from that of the same concave etched by a different etching amount. In contrast, the diameter of a fine particle does not depend on the etching amount. As a result, if a beam is applied to the same point of a substrate subject to two different etching amounts and if reflected beams are different, then the point is considered as a defect point. A more precise evaluation of a substrate can be achieved by applying a beam to the same point of the substrate surface at different incident angles. Namely, a substrate can be more correctly evaluated by counting the number of light scattering bodies on the substrate surface by applying a beam at different incident angles. For such beam application, it is necessary to calibrate a measurement apparatus by using a standard substrate. It is preferable to use a standard substrate having on the surface thereof concaves of a predetermined density and size generated by processing a semiconductor substrate with alkaline solution. Specifically, if a semiconductor substrate is processed with alkali solution, the size and density of defects on the substrate are determined depending upon the etching amount. By setting a proper etching amount, it is possible to generate defects on a substrate having a predetermined size and density. Such a substrate is suitable for a standard substrate to be used by calibration.

According to the present invention, a semiconductor substrate is etched, and thereafter the surface thereof is checked by using a light beam. As a result, the defect on the surface can be located in accordance with the etching amount, allowing a proper evaluation of the substrate. Furthermore, a beam is applied to the same point of a substrate surface at different angles. It is therefore possible to detect and evaluate a defect more reliably from a light intensity. Such a beam application apparatus is required to be calibrated by using a standard substrate having on the surface thereof concaves of a predetermined size and density. By processing a semiconductor substrate, a standard substrate for calibration can be obtained.

DESCRIPTION OF THE PREFERRED EMBODIMENTS

Preferred embodiments of the present invention will be described with reference to the accompanying drawings.

Figure 1:
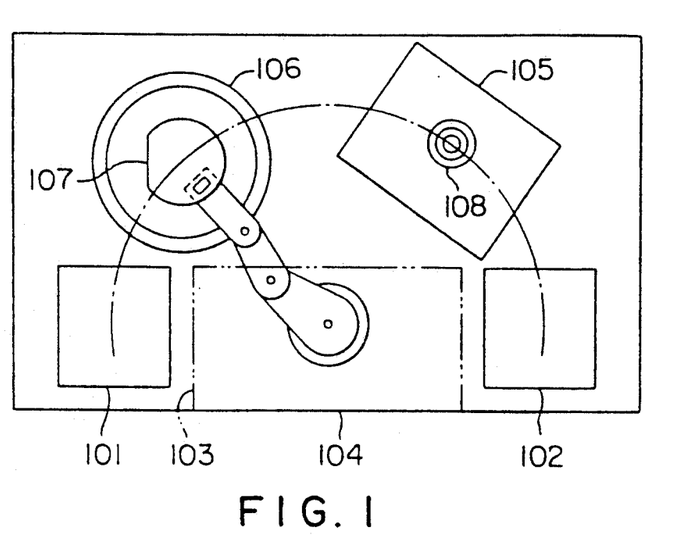
FIG. 1 is a plan view showing an apparatus according to the first embodiment of the present invention.

FIG. 1 is a plan view briefly showing an evaluation apparatus according to an embodiment of the present invention.

Figure 2:
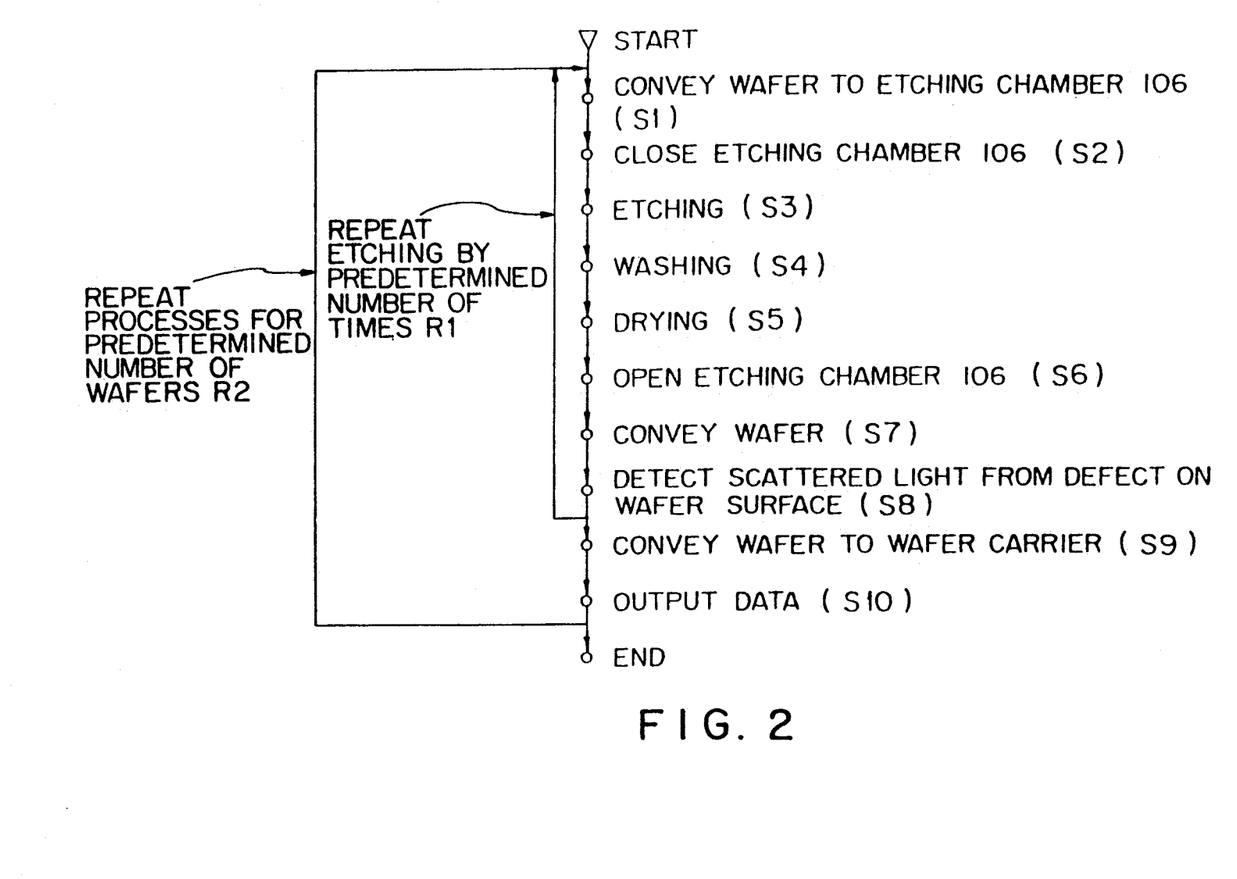
FIG. 2 shows an operation flow of the apparatus shown in FIG. 1.

In FIG. 1, reference numeral 101 represents a carrier for wafers to be measured, and reference numeral 102 represents a carrier for measured wafers. Prior to measurement, wafers are set on the carrier 101, and the carrier 102 is set with nothing placed thereof. For measurement, one of wafers on the carrier 101 is picked up by a wafer conveyor 104, and the wafer is placed on a wafer chuck within an etching chamber 106. The etching chamber 106 is made of PTFE inactive to chemicals, and has a disk type wafer stage and a cover. This cover closes air-tightly the chamber 106, or opens it. The etching chamber 106 is provided with a liquid drainage port, a chemicals supply port, a pure water supply port, and a high purity $N_2$ gas supply port. As shown in FIG. 2, a wafer is subject to etching (S3), washing (S4), and crying (S5). As an etching liquid, $NH_4OH:H_2O_2:H_2O = 1:1:5$ is used.

The etched and dried wafer 107 is set to a defect detecting apparatus 105 by the conveyor 104 (S6, S7). The wafer 107 is fixed on a vacuum chuck 108 within the defect detecting apparatus 105, to detect defects on the wafer surface, the detects having been made visual by the etching (S8). The apparatus 105 has a He-Ne laser. A laser beam from this laser is radiated on the wafer surface. The laser beam is scattered by defects on the wafer surface. The scattered laser beams are received by a photomultiplier to convert them into electric signals having the intensity corresponding to the scattered laser beams. By detecting the original radiation positions of scattered beams, it is possible to map the scattered light quantities on the coordinate system of the wafer surface. This mapping data is stored in a memory of a processor 103. The steps (S1 to S8) from the etching to the defect detecting may be repeated a desired number of times by a program (R1). The defect-detected wafer is sent to the wafer carrier 102. Thereafter, the data is outputted from the processor 103 (S10). The processor 103 also evaluates the wafer using the outputs from the photomultiplier. The steps S1 to S10 are repeated for other wafers (R2). Preferably the above evaluation is carried out under the condition of 10,000/ft$^3$ fine particles equal to or greater than 0.5 $\mu$m.

By using the evaluation apparatus constructed as above, a single wafer can be automatically etched and evaluated a plurality of times, reducing labor of an operator. Repetitive etching enlarges visual defects on the wafer surface. However, although the number of fine particles attached on the wafer surface changes more or less, the size thereof will not change. Therefore, it is possible to determine whether light scattering substance at a particular coordinate point is a fine particle or a defect, based on the mapping data obtained at the time of detecting defects. This becomes easier the more the etching is repeated. In this manner, a wafer can be evaluated from the number and size of defects.

Figure 3:
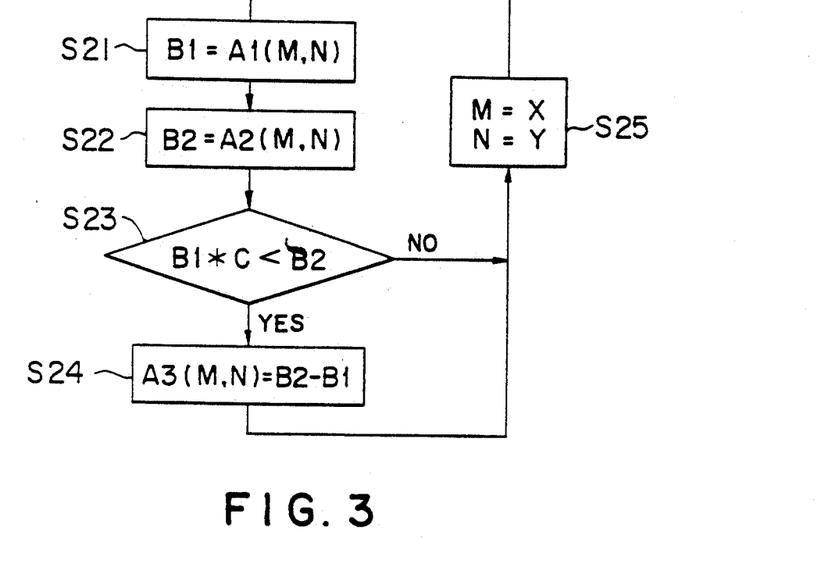
FIG. 3 is a flow chart showing the procedure of discriminating between fine particles and defects on a wafer surface.

FIG. 3 shows an example of an evaluation flow. In FIG. 3, $A_n (X, Y)$ represents a scattered light intensity after repeating the etching step (S3) n times. This intensity is proportional to the diameter of a particle, groove, or the like causing scatter. C represents a variation coefficient. Whether a light scattering body is a defect or a fine particle can be discriminated in accordance with whether a scattered light intensity increases (Yes at S23) or not (No at S23) irrespective of the number of etching steps.

In the above embodiment, as an etching liquid, a liquid containing choline and $H_2O_2$ may be used. If the etching time period is controllable, the etching step may be carried out for a predetermined time period without repeating the wafer etching step.

Instead of a He-Ne laser for detecting defects, other laser and electron beam sources may be used which can detect desired fine convex and concave. It is apparent that a probe is not limited only to an optical probe.

Figure 4:
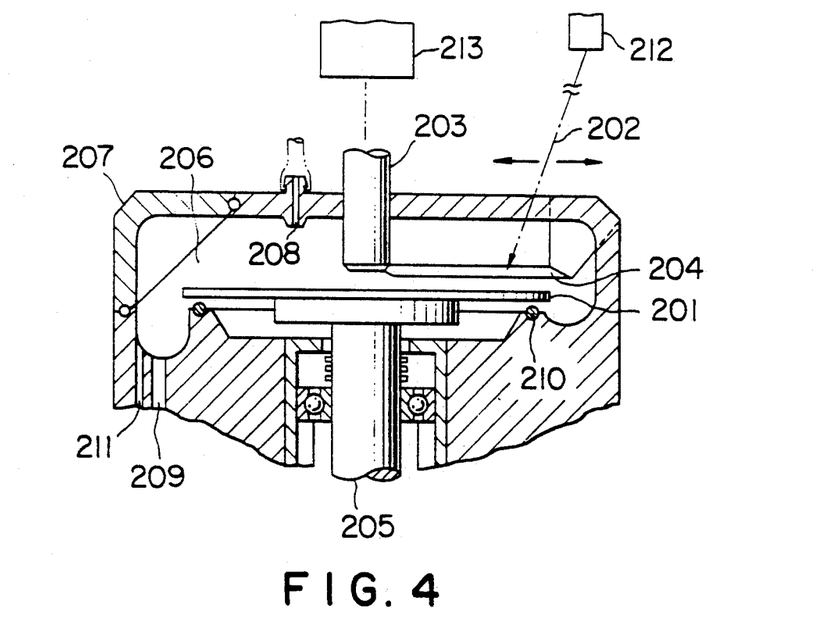
FIG. 4 is a cross sectional view of an apparatus according to the second embodiment of the present invention.

FIG. 4 shows an apparatus integrally mounting the etching chamber 106 and light scatter type defect detecting apparatus 105 shown in FIG. 1. A wafer 201 to be measured is held by a vacuum chuck 205 and rotated at a desired number of revolutions. An etching chamber 206 containing the wafer 201 is provided with a purge/dry gas port 208, a laser beam incident window 204, a scattered light detector 203, an etching liquid supply port 209, and a liquid drainage/air exhaust port 211. Reference numeral 212 represents a laser, and reference numeral 213 represents a processor/evaluator means.

Within this chamber 206, the steps from the etching, wafer drying to defect detecting can be continuously carried out. Therefore, a change in number of fine particles, which is present more or less because of repetitive etching steps, can be reduced as compared to the apparatus shown in FIG. 1, allowing more precise defect detecting.

The wafer 201 is housed within, or taken out of, the chamber 206 by a wafer conveyor by opening and closing a upper lid 207 of the chamber 206. As the chuck 205 lowers, the wafer 201 fixed to it becomes in air-tight contact with an O-ring. Next, an etching liquid is supplied via the etching liquid supply port 209 to etch the wafer 201. After etching, pure water is supplied via a pure water supply port (not shown) to wash the wafer 201. Thereafter, liquid is drained and the chuck 205 is raised to detach the wafer 201 from the O-ring. While the wafer 201 is rotated, a dry air or a high purity gas such as $N_2$ and $A_n$ is applied to the wafer 201 from the gas supply port 208 to dry the wafer 201. After drying the wafer 201, a laser beam is radiated to the wafer 201 to detect scattered laser beams and detect defects. The defect detecting method is the same as described above. It is apparent that the laser incident window 204, detector 203 and the like be made of material sufficiently resistant to the etching liquid. With this arrangement, as described previously, a change in number of fine particles on the wafer 201 during measurement can be reduced, allowing high precision defect detecting.

As described above in detail, this method etches a wafer and detects light scattering bodies a plurality of times. Therefore, it is possible to discriminate between defects which become large as the etching amount increases, and fine particles not related to the etching amount. The number of defects can also be counted. In this manner, crystal defects near the wafer surface influencing manufacturing yield of semiconductor devices can be very easily evaluated without thermal treatment.

Next, another embodiment will be described. In checking the processed wafer surface with a laser beam, it is very important that a laser beam is applied to the wafer surface at a plurality of different incident angles.

Figure 5A:
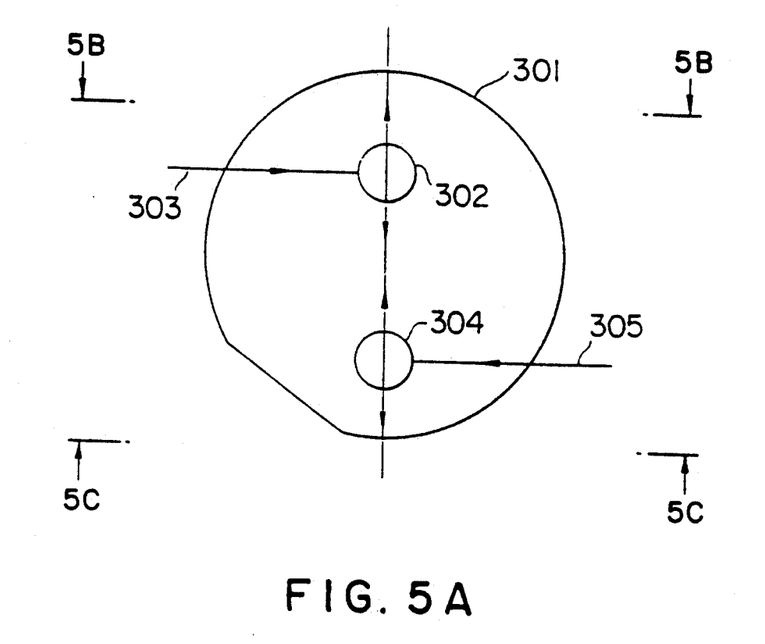
FIGS. 5A to 5C are conceptual diagrams showing the third embodiment.
Figure 5B:
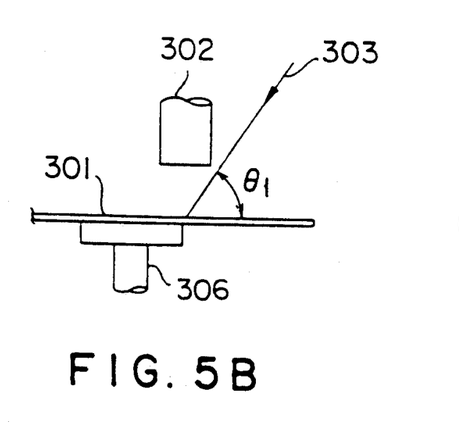
Figure 5C:
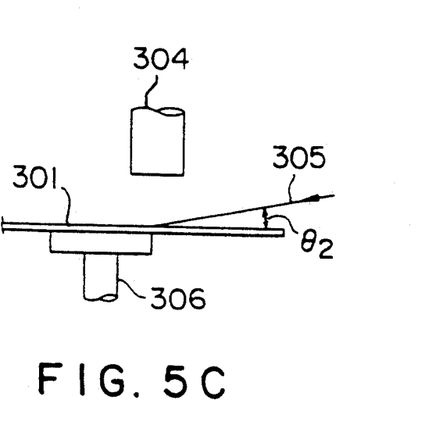

FIGS. 5A to 5C show an example of an apparatus which applies laser beams 303 and 305 at two different incident angles $\theta_1$ and $\theta_2$.

In FIGS. 5A to 5C, reference numeral 301 represents a wafer, reference numerals 302 and 304 represent scattered light detectors, and reference numerals 303 and 305 represent laser beams. Reference numeral 306 represents a rotatable wafer chuck which is movable in the direction parallel to the wafer surface. The scattered light detector 302 detects scattered light beams of the laser beam 303, and the scattered light detector 304 detects scattered light beams of the laser beam 305. The measurement method will be described below. The wafer 301 to be measured is fixed to the wafer chuck 306 which is then rotated at a predetermined number of revolutions. Next, the laser beam 303 is applied to the peripheral area of the wafer 301, and the scattered light detector 304 is moved to the position just above the radiation area. When a scattered light is detected, the coordinate position on the wafer at the detected area is determined from the motion amount of the wafer chuck 306 in the direction along the wafer surface, and stored in a memory. The map (FIG. 6) of scattered light intensities by the laser beam 303 shown in FIGS. 5A and 5B is formed as shown in Table 1.

TABLE 1

Figure 6:
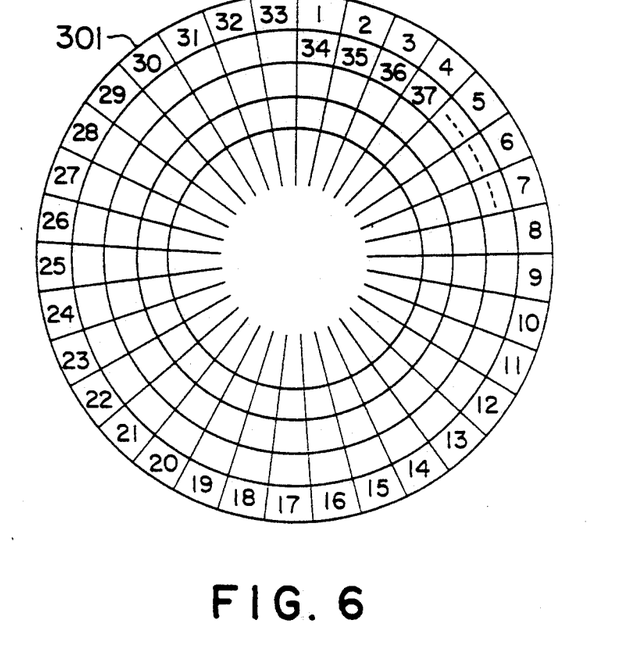
FIG. 6 is a conceptual diagram showing a map of a wafer surface.

| point of wafer | 1 | 2 | 3 | 4 | 5 | 6 | 7 | 8 | 9 | 10 | ... |
|---|---|---|---|---|---|---|---|---|---|---|---|
| scattered light intensity | 0 | 0 | 1 | 0 | 0 | 0 | 5 | 1 | 0 | 2 | ... |

Specifically, when a scattered light is detected at a certain coordinate position, a scattered light intensity value is stored in association with the coordinate position. The map of scattered light intensities by the laser beam 305 shown in FIGS. 5A and 5C is also stored in the similar manner as above. In this case, the scattered light intensities can be detected in association with the coordinate positions same as the laser beam 303, in accordance with signals from the motor for the wafer chuck 306.

Figure 7:
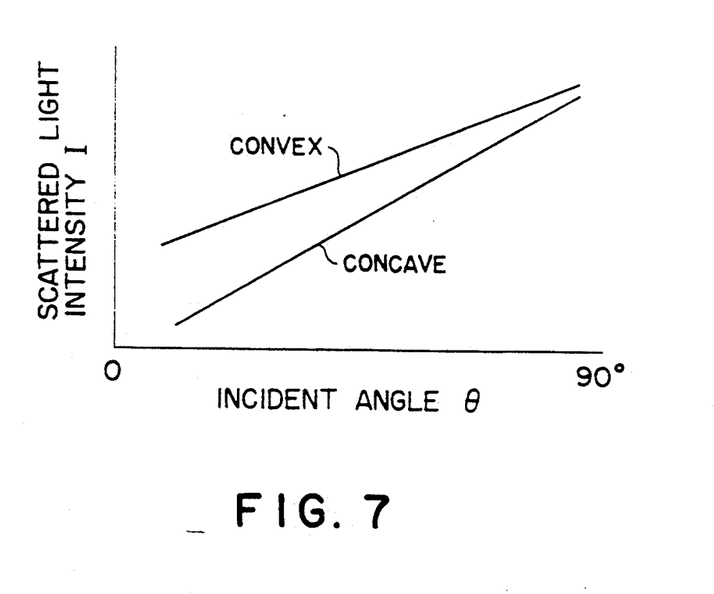
FIG. 7 is a graph conceptually showing the dependency of scattered light intensity upon a scattering body shape, relative to a beam radiation angle.

After scanning the entire surface of the wafer 301 with the laser beams 303 and 305, the scattered light intensities by the two laser beams 303 and 305 are compared with each other. As shown in FIG. 7, a scattered light from a concave is depends on a laser beam incident angle greater than that from a convex. Therefore, a ratio between scattered light beams from the same concave by two laser beams having different incident angles is larger than that between scattered light beams from the same convex. Furthermore, as shown in Table 2, the diameter of a light scattering body is measured by a scattered light detector for a laser beam incident angle $\theta$.

TABLE 2

| | small diameter | | large diameter | |
|---|---|---|---|---|
| | convex | concave | convex | concave |
| scattered light intensity | weak | weak | strong | strong |
| ratio of scattered light intensities | small | large | small | large | where the intensity ratio = $I\theta_1/I\theta_2$ ($\theta_1 > \theta_2$).

For determining the shape (convex or concave) of a light scattering body, the scattered light intensity ratio I is used where $I = I\theta_1/I\theta_2$ ($\theta_1 > \theta_2$, refer to FIGS. 5A to 5C). It is therefore possible to evaluate the shape and size of a light scattering body. It is apparent that the distribution of light scattering bodies can be outputted from the maps such as shown in FIG. 6.

The apparatus described above in detail can evaluate the crystal property of a semiconductor wafer. As described previously, prior to detecting scattered light beams, a wafer is processed under the predetermined conditions. Specifically, the etching liquid of $NH_4OH:H_2O_2:H_2O = 1:1:5$ is maintained at 70° C. and a wafer is dipped in this liquid for ten minutes. Thereafter, the wafer is washed for ten minutes while flowing pure water. With such processing, fine defects present on the wafer surface are selectively etched, generating fine defects (etch pits) about 0.1 $\mu$m. Obviously, it is desired that the etching liquid and pure water do not contain fine particles at all. However, in practice, some fine particles attach the wafer surfaces which were contained within a processing vessel, a dryer, chemicals, and pure water. Therefore, it is necessary to discriminate between visual etch pits and fine particles. Such discrimination can be achieved by the embodiment apparatus.

As described above in detail, this apparatus applies a laser beam to the same area of a semiconductor wafer at least at two different incident angles. The intensity of a scattered light beam changes with the shape (concave and convex) of a light scattering body. Therefore, the size of a light scattering body can be determined using a laser beam having either a high incident angle or a low incident angle. Furthermore, it is possible to determine whether a light scattering body is a concave or a convex, in accordance with a ratio of a scattered light intensity by a high incident angle to a scattered light intensity by a low incident angle. It is therefore possible to easily measure the number and distribution of fine defects in the form of visual etch pits of a semiconductor wafer exposed in an atmosphere equal to or higher than pH 8 as a pre-process.

The above-described apparatus (light scatter type wafer surface particle measuring apparatus) is required to make sensitivity calibration in advance. For sensitivity calibration, conventionally, a standard wafer has been used which has a mirror surface coated with standard particles made of polystyrene latex (trade name). This standard wafer coated with standard particles made of polystyrene latex has the following problems:

1) Uniform coating is difficult, particularly coating at a low density area is almost impossible. No standard wafer guarantees a particle density.

2) Susceptible to change with time by custody environments or during handling.

3) Standard particles are manually coated, taking a time and causing density variations.

4) Coated standard particles cannot be visually discriminated from particles attached to the wafer surface after coating, resulting in low reliability of the standard wafer.

It is desirable to use a standard wafer proposed by the present inventors in place of a conventional standard wafer. The standard wafer proposed by the present inventors has concaves on the wafer surface. This standard wafer is manufactured using the technical feature that defects on a silicon wafer surface are selectively etched by alkali-based washing chemical liquid and that the defect density can be controlled as desired by a crystal substrate manufacturing method. The etching speed of a silicon wafer in washing chemical liquid can be controlled within the range of 0 to 100 angstroms/minute. It is therefore easy to control the size of a concave (corresponding to particle size).

It is also possible to control the number of concaves (corresponding to particle density) generated by etching, within a range of 0 to 100 concaves/cm$^2$ by the crystal substrate manufacturing method.

A newly proposed standard wafer will be detailed below.

Figure 8A:
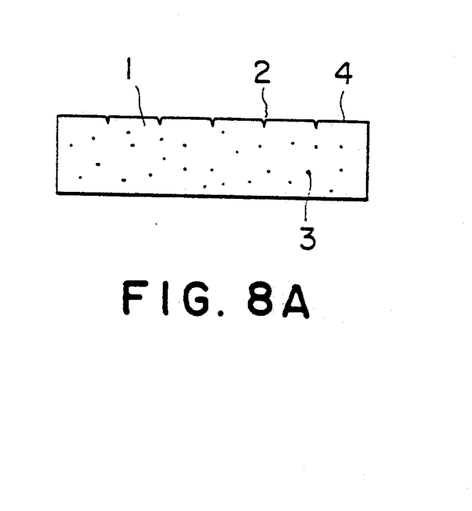
FIGS. 8A and 8B are cross sectional views showing steps of manufacturing a standard wafer.
Figure 8B:
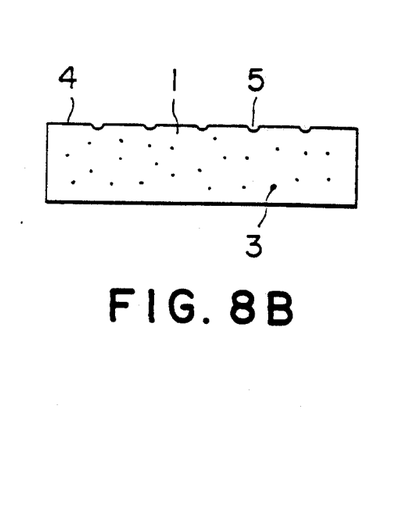

The schematic cross sectional views of a newly proposed standard wafer before and after alkaline etching are shown in FIGS. 8A and 8B. FIG. 8A is a cross sectional view before etching, and FIG. 8B is a cross sectional view after etching.

Within a silicon wafer 1, there are precipitated substances 3 having oxygen, carbon, metal impurities as nuclei which were generated by thermal treatment at the time of growing silicon monocrystal or after the wafer forming process. The density of precipitated substances is within the range of 0 to $10^9$ substances/cm$^3$, depending upon the monocrystal growth condition, oxygen concentration, carbon concentration, metal impurity quality, thermal treatment condition, and the like.

Figure 10:
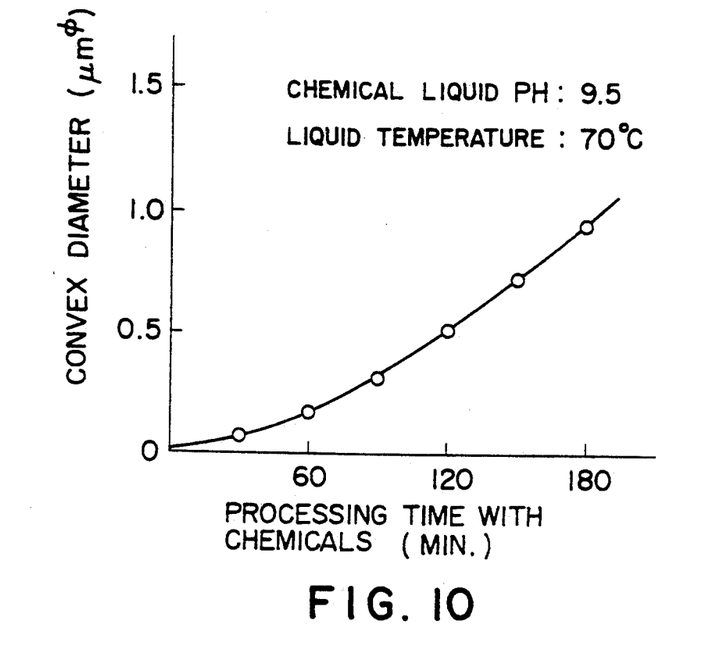
FIG. 10 is a graph showing the relation between a concave diameter and a wafer processing time with chemicals.
Figure 11:
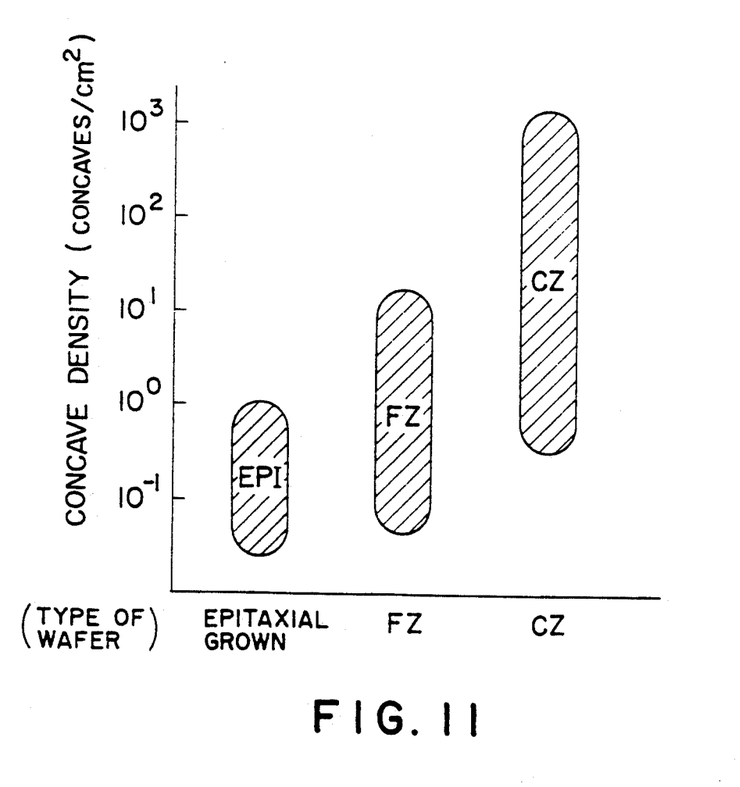
FIG. 11 is a graph showing the relation between a concave density and a type of wafer crystal.

Precipitated substances 2 are also present on the wafer surface 4 after polishing. In this condition, a laser beam applied to the surface will not produce scattered light because the size of each precipitated substance 2 is small. This wafer cannot be used therefore as a standard wafer by a particle measurement apparatus. However, these precipitated substances 2 have a property of being etched at a high selection factor equal to or greater than 100 relative to silicon, by using alkali-based chemicals. By applying mirror polishing with alkali-based mechanochemical polishing agent and by using processing liquid of ammonium solution/hydrogen peroxide water/water (example of volume ratio 1:1:4), precipitated substances 2 are selectively etched to generate concaves 5. The size of concaves 5 can be controlled by the wafer processing time with alkali-based chemical liquid. FIG. 10 shows the relation between the size (diameter) of a concave and the wafer processing time with chemical liquid. The density of concaves differ depending upon the type of wafer crystal as described previously. The concave density on a wafer crystal has the characteristics of FZ<CZ, Epi<CZ, low oxygen concentration<high oxygen concentration, and the like (refer to FIG. 11).

Figure 9:
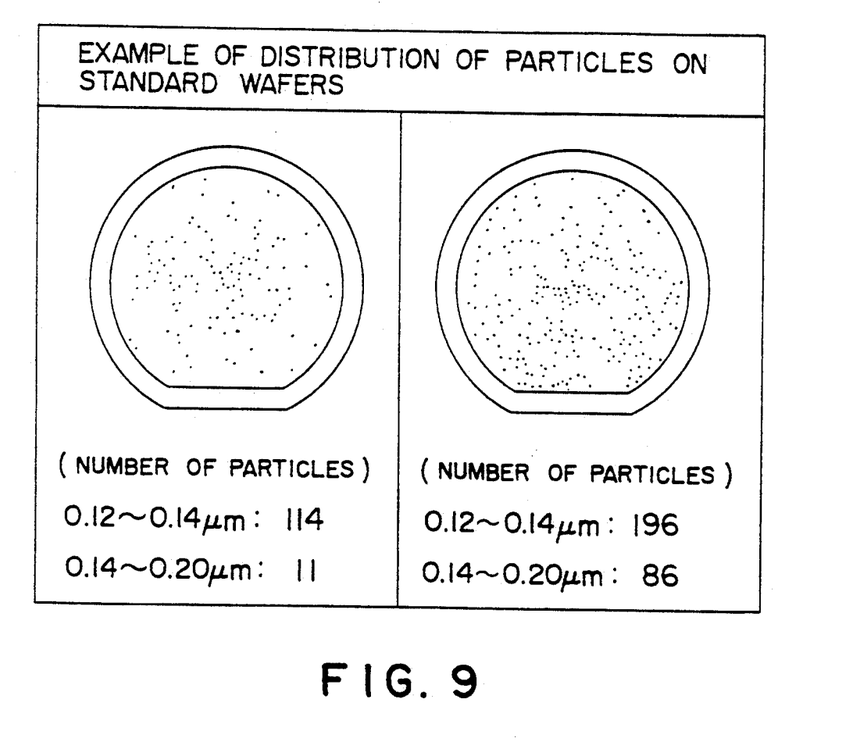
FIG. 9 is a plan view showing examples of distributions of particles (concaves) on standard wafers.

FIG. 9 shows the measurement of a standard wafer manufactured in the above-described manner, using a particle measurement apparatus (corresponding to 0.1 $\mu$m).

Standard wafers proposed by the present inventors have the following advantages:

1) When a laser beam is applied to a concave on a standard wafer, scattered light can be obtained as in the case of standard particles coated on a wafer surface. The size of a concave can be selected as desired by a wafer processing time with alkali-based chemical liquid, and the density concaves can be selected as desired by the crystal manufacturing method or wafer thermal treatment conditions. Therefore, the size of a particle and the density of particles can be reliably set, although the latter was impossible to be set in the past.

2) Mass production is possible, providing a large number of standard wafers.

3) Contaminations and particles on a standard wafer surface attached during custody or handling can be removed by ordinary chemical washing. Thus, the particle density and size does not change with time as was the case of a conventional standard wafer made by a standard particle coating method. The reliability of a standard wafer can thus be improved.

What is claimed is:

1. A method of detecting a defect on the surface of a semiconductor substrate, comprising:
   a first etching step of etching a semiconductor substrate by a first etching amount;
   a first check step of applying a beam to the surface of said substrate underwent said first etching step, and detecting a first reflected beam;
   a second etching step of etching said substrate etched by said first etching amount, by an additional etching amount, to make the total etching amount a second etching amount;
   a second check step of applying said beam to the surface of said substrate underwent said second etching step, and detecting a second reflected beam; and
   a calculation step of calculating the relation between said first and second reflected beams.

2. A method according to claim 1, wherein said calculation step compares the intensity of said first reflected beam with the intensity of said second reflected beam.

3. A method according to claim 2, wherein said first and second check steps sequentially apply said beam to a plurality of fine points on said substrate, and receive a reflected beam from each said fine point in association with the coordinate value of each said fine point.

4. A method according to claim 3, wherein said first and second check steps receive light scattered beams as said first and second reflected beams.

5. A method according to claim 4, wherein said calculation step compares said first and second reflected beams from each said fine point on said substrate, and determines whether each said fine point has a defect, in accordance with whether the scattered light intensity of said second reflected beam becomes higher than that of said first reflected beam.

6. A method according to claim 5, wherein said first and second etching steps etch said semiconductor substrate using alkaline solution equal to or higher than pH 8.

7. A method according to claim 5, wherein said first and second etching steps use an etching liquid containing $NH_4OH$, $H_2O_2$, and $H_2O$.

8. A method according to claim 5, wherein said first and second etching steps use an etching liquid containing choline and $H_2O$.

9. A method according to claim 5, wherein a laser beam is used as said beam.

10. A method according to claim 5, wherein a Ne-He laser beam is used as said beam.

11. A method according to claim 5, wherein an electron beam is used as said beam.

12. A method according to claim 5, wherein said first and second check steps are executed under the conditions of 10,000 fine particles/ft$^3$, said particle being equal to or larger than 0.5 $\mu$m.

13. An apparatus for detecting a defect on the surface of a semiconductor substrate, comprising:
   an etching chamber for accommodating a semiconductor substrate to be measured;
   an etching liquid supply port for supplying an etching liquid to said chamber;
   an etching liquid drainage port for draining said etching liquid from said chamber;
   a beam radiating means for radiating a beam onto the surface of said substrate;
   reflected beam detecting means for detecting a reflected beam from said substrate; and
   calculating means for calculating the relation between an etching amount and an intensity of said reflected beam in accordance with an output from said reflected beam detecting means.

14. An apparatus according to claim 13, wherein said calculation means compares the intensities of said reflected beams from said substrate etched by different etching amounts.

15. An apparatus according to claim 14, further comprising means for rotating said substrate about an axis perpendicular to said substrate.

16. An apparatus according to claim 15, wherein said reflected beam detecting means receives a scattered beam as said reflected beam.

17. An apparatus according to claim 16, wherein said calculating means determines whether there is a defect, in accordance with whether the intensity of said reflected beam from said substrate etched by a larger one of said different etching amounts becomes higher than that of said reflected beam from said substrate etched by a smaller one of said different etching amounts.

18. A method of detecting a defect on the surface of a semiconductor substrate, comprising:
    a pre-processing step of pre-processing a semiconductor substrate;
    a check step of applying a plurality of light beams to the same point on the surface of said pre-processed semiconductor substrate at different incident angles, and detecting each scattered light for each said different incident angle; and
    a calculation step of determining whether there is a defect on the surface of said semiconductor substrate, in accordance with the intensities of said scattered light for said different incident angles obtained by said check step.

19. A method according to claim 18, wherein said calculation step determines, in accordance with a ratio of two scattered light from the same point on said substrate caused by two said beams having said different incident angles, whether said point is a concave or convex.

20. A method according to claim 19, wherein said pre-processing step dips said semiconductor substrate for ten minutes in a liquid containing $NH_4OH:H_2O_2:H_2O = 1:1:5$ maintained at 70° C., and thereafter washed said substrate with pure water.

* * * * *